(12) United States Patent
Hourmand et al.

(10) Patent No.: US 9,592,340 B2
(45) Date of Patent: *Mar. 14, 2017

(54) AUTO-INJECTOR HAVING DRIVE SPRING SWITCHING GROUND FROM DISTAL TO PROXIMAL ENDS OF MAIN BODY BETWEEN PUSHING AND RETRACTING SYRINGE NEEDLE

(71) Applicant: Sanofi-Aventis Deutschland GmbH, Frankfurt am Main (DE)

(72) Inventors: Yannick Hourmand, Cambridgeshire (GB); Timothy Donald Barrow-Williams, Hertfordshire (GB); Matthew Ekman, Cheshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 168 days.

This patent is subject to a terminal disclaimer.

(21) Appl. No.: 13/962,323

(22) Filed: Aug. 8, 2013

(65) Prior Publication Data

US 2013/0345643 A1 Dec. 26, 2013

Related U.S. Application Data

(63) Continuation of application No. 13/806,325, filed as application No. PCT/EP2011/060507 on Jun. 22, 2011, now abandoned.

(30) Foreign Application Priority Data

Jun. 28, 2010 (EP) .................................. 10167495
Jun. 28, 2010 (EP) .................................. 10167500
Oct. 14, 2010 (EP) .................................. 10187528

(51) Int. Cl.
*A61M 5/20* (2006.01)
*A61M 5/32* (2006.01)

(52) U.S. Cl.
CPC ........ *A61M 5/2033* (2013.01); *A61M 5/3232* (2013.01); *A61M 5/3257* (2013.01); *A61M 2005/206* (2013.01); *A61M 2005/208* (2013.01)

(58) Field of Classification Search
CPC .. A61M 5/3243; A61M 5/3219; A61M 5/322; A61M 5/3221; A61M 5/3202;
(Continued)

(56) References Cited

U.S. PATENT DOCUMENTS 2,752,918 A * 7/1956 Uytenbogaar ...... A61M 5/2033
604/136
3,320,955 A * 5/1967 Sarnoff ............... A61M 5/2033
604/138
(Continued)

FOREIGN PATENT DOCUMENTS

| GB | 2461088 | 12/2009 |
| GB | 2467637 | 8/2010 |
| WO | 2009/127861 | 10/2009 |

OTHER PUBLICATIONS

International Search Report for Int. App. No. PCT/EP2011/060507, completed Dec. 1, 2011.

*Primary Examiner* — Bhisma Mehta
*Assistant Examiner* — Matthew A Engel
(74) *Attorney, Agent, or Firm* — Fish & Richardson P.C.

(57) ABSTRACT

An auto-injector for administering a dose of a liquid medicament (M) is presented comprising an elongate housing arranged to contain a syringe with a hollow needle and a stopper for sealing the syringe and displacing the medicament (M), the housing having a distal end (D) and a proximal end (P) with an orifice intended to be applied against an injection site, wherein the syringe is slidably arranged with respect to the housing. The auto-injector contains a spring means capable of, upon activation, pushing (Continued)

the needle from a covered position inside the housing into an advanced position through the orifice and past the proximal end (P), operating the syringe to supply the dose of medicament (M), and retracting the syringe with the needle into the covered position after delivering the medicament (M). There is also an activating means arranged to lock the spring means in a pressurized state prior to manual operation.

15 Claims, 2 Drawing Sheets

(58) Field of Classification Search
CPC .......... A61M 5/31535; A61M 5/31583; A61M 5/1454; A61M 2005/31508
USPC ................. 604/134–137, 187, 192, 196–198
See application file for complete search history.

(56) References Cited

U.S. PATENT DOCUMENTS

| | | | | |
|---|---|---|---|---|
| 3,880,163 A | * | 4/1975 | Ritterskamp | A61M 5/2033 604/136 |
| 4,627,835 A | * | 12/1986 | Fenton, Jr. | A61M 5/1456 128/DIG. 1 |
| 5,042,977 A | * | 8/1991 | Bechtold et al. | 604/134 |
| 5,188,613 A | * | 2/1993 | Shaw | A61M 5/3234 604/111 |
| 5,242,400 A | * | 9/1993 | Blake, III | A61M 5/322 604/110 |
| 5,364,369 A | * | 11/1994 | Reynolds | A61J 1/2089 604/187 |
| 5,385,551 A | * | 1/1995 | Shaw | A61M 5/3234 604/110 |
| 5,478,316 A | * | 12/1995 | Bitdinger | A61M 5/2033 604/134 |
| 5,503,627 A | * | 4/1996 | McKinnon | A61M 5/24 604/68 |
| 5,599,309 A | * | 2/1997 | Marshall | A61M 5/2033 604/117 |
| 5,709,662 A | * | 1/1998 | Olive | A61M 5/2033 604/110 |
| 6,159,181 A | * | 12/2000 | Crossman | A61M 5/2033 604/134 |
| 6,186,980 B1 | * | 2/2001 | Brunel | A61M 5/3202 604/110 |
| 7,361,160 B2 | * | 4/2008 | Hommann et al. | 604/198 |
| 2002/0095120 A1 | * | 7/2002 | Larsen et al. | 604/187 |
| 2005/0261634 A1 | * | 11/2005 | Karlsson | 604/197 |
| 2007/0021715 A1 | * | 1/2007 | Kohlbrenner et al. | 604/67 |
| 2007/0093761 A1 | * | 4/2007 | Veasey | A61M 5/31546 604/207 |
| 2009/0275916 A1 | * | 11/2009 | Harms et al. | 604/506 |
| 2010/0036319 A1 | * | 2/2010 | Drake | A61J 1/1406 604/135 |
| 2011/0092954 A1 | * | 4/2011 | Jennings | A61M 5/2033 604/506 |
| 2011/0098647 A1 | * | 4/2011 | Jennings | A61M 5/1782 604/154 |
| 2011/0130743 A1 | * | 6/2011 | Jennings | A61M 5/1782 604/506 |
| 2012/0283698 A1 | * | 11/2012 | Millerd | A61M 5/2429 604/506 |
| 2013/0060232 A1 | * | 3/2013 | Adlon | A61M 5/2066 604/506 |
| 2013/0150801 A1 | * | 6/2013 | Ekman | A61M 5/2033 604/198 |
| 2013/0310759 A1 | * | 11/2013 | Hourmand | A61M 5/2033 604/198 |
| 2014/0221974 A1 | * | 8/2014 | Bechmann | A61M 5/2033 604/506 |

* cited by examiner

AUTO-INJECTOR HAVING DRIVE SPRING SWITCHING GROUND FROM DISTAL TO PROXIMAL ENDS OF MAIN BODY BETWEEN PUSHING AND RETRACTING SYRINGE NEEDLE

CROSS REFERENCE TO RELATED APPLICATIONS

The present application is a continuation of U.S. patent application Ser. No. 13/806,325, filed Dec. 21, 2012, which is a U.S. National Phase Application pursuant to 35 U.S.C. §371 of International Application No. PCT/EP2011/060507 filed Jun. 22, 2011, which claims priority to European Patent Application No. 10167495.0 filed Jun. 28, 2010, European Patent Application No. 10167500.7 filed Jun. 28, 2010, and European Patent Application No. 10187528.4 filed Oct. 14, 2010. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The post published European Patent Application No. 092908482 discloses an auto-injector for administering a dose of a liquid medicament, comprising:

an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing, spring means capable of, upon activation:

pushing the needle from a covered position inside the housing into an advanced position through the orifice and past the proximal end, operating the syringe to supply the dose of medicament, and retracting the syringe with the needle into the covered position after delivering the medicament, activating means arranged to lock the spring means in a pressurized state prior to manual operation and capable of, upon manual operation, releasing the spring means for injection, The spring means is a single compression spring arranged to be grounded at a distal end in the housing for advancing the needle and for injecting the dose of medicament via a plunger and wherein the compression spring is arranged to have its ground in the housing switched to its proximal end for retracting the syringe.

SUMMARY

It is an object of the present invention to provide an auto-injector with simplified handling.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention an auto-injector for administering a dose of a liquid medicament comprises:

an elongate main body arranged to contain a syringe with a hollow needle and a stopper for sealing the syringe and displacing the medicament, the main body having a distal end and a proximal end with an orifice intended to be applied against an injection site, wherein the syringe is slidably arranged with respect to the main body, spring means capable of, upon activation:

pushing the needle from a covered position inside the main body into an advanced position through the orifice and past the proximal end, operating the syringe to supply the dose of medicament, and retracting the syringe with the needle into the covered position after delivering the medicament, activating means arranged to lock the spring means in a pressurized state prior to manual operation and capable of, upon manual operation, releasing the spring means for injection.

According to the invention the spring means is a single drive spring in the shape of a compression spring arranged to be grounded at a distal end in the main body for advancing the needle and for injecting the dose of medicament. The force of the drive spring is forwarded to the needle and/or the syringe via a plunger. The drive spring is arranged to have its ground in the main body switched to its proximal end for retracting the syringe when the injection of the medicament is at least nearly finished.

The single drive spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the drive spring is grounded the proximal end moves the syringe forward for inserting the needle and carries on to the injection by pushing on the stopper. When the injection is at least nearly finished the drive spring bottoms out at its proximal end, resulting in the proximal end being grounded in the main body. At the same time the distal end of the drive spring is released from its ground in the main body. The drive spring is now pulling the syringe in the opposite direction.

According to the invention the activating means comprises a trigger button in the shape of a wrap-over sleeve button arranged over the distal end of the auto-injector. The trigger button extends at least almost over the whole length of the auto-injector. The trigger button is arranged to release the drive spring upon translation in proximal direction. In order to trigger an injection the auto-injector has to be pressed against an injection site, e.g. a patient's skin. A user, e.g. the patient or a caregiver, grabs the wrap-over sleeve button with their whole hand and pushes against the injection site. Consequently, the trigger button translates in proximal direction and releases the drive spring for starting the injection cycle. The auto-injector according to the invention is particularly well suited for people with dexterity problems since, as opposed to conventional art auto-injectors, triggering does not require operation of small buttons by single fingers. Instead, the whole hand is used.

The auto-injector according to the invention has a particularly low part count compared to most conventional auto-injectors. The use of just one drive spring reduces the amount of metal needed and thus consequently reduces weight and manufacturing costs.

In one embodiment of the auto-injector at least one clip is arranged in the main body. The clip is arranged to lock the drive spring in the as delivered configuration. Furthermore, the clip is arranged to be unlocked under load of the drive spring by flexing outwards. The sleeve of the trigger button has a locking section with a reduced diameter arranged to prevent the clip from flexing outwards in the as delivered configuration, i.e. when the trigger button is not pushed. When the trigger button and the locking section are translated in proximal direction by being pushed onto the injection site the clip comes clear of the locking section and may now flex outwards under load of the drive spring thus releasing the drive spring for the injection. The clip and/or a component under load of the drive spring may have ramps for flexing the clip outwards.

In a preferred embodiment an interlock sleeve is telescoped with the proximal end of the main body, the interlock sleeve translatable in longitudinal direction between a proximal position and a distal position and biased in proximal direction in a manner to protrude from the main body in the proximal position, wherein in its proximal position the interlock sleeve is arranged to prevent translation of the syringe in proximal direction from its retracted position with respect to the main body and wherein the interlock sleeve in its distal position is arranged to allow translation of the syringe in proximal direction.

In the delivered state of the auto-injector the interlock sleeve is in its proximal position protruding from the proximal end of the main body. The syringe and needle are in their retracted position. In order to trigger an injection the auto-injector has to be pressed with its proximal end, i.e. the interlock sleeve against the injection site in a manner to translate the interlock sleeve in distal direction into the main body. Thus the syringe is unlocked from the main body may now translate so as to move the needle into its advanced position for piercing the patient's skin. Before the syringe and needle actually translate in proximal direction the activating means, i.e. the wrap-over sleeve trigger button has to be operated so as to release the drive spring. Both actions translating the interlock sleeve in distal direction and translating the trigger button in proximal direction require the user to grab the trigger button and press the auto-injector against the injection site. In order to ensure, that the interlock sleeve translates before the trigger button, the interlock sleeve may have a weaker spring means for biasing it than the trigger button. These two translations appear to the user like a two step translation with an increase in force between the steps.

In another preferred embodiment at least one resilient second clip is arranged on the main body. The second clip is biased so as to block the trigger button from being translated in proximal direction when the second clip is relaxed. In its distal position the interlock sleeve is arranged to push the clip against its bias so as to decouple it from the trigger button thus allowing translation of the trigger button in proximal direction. This embodiment ensures a sequenced operation with a higher reliability than the two differently strong spring means. The interlock sleeve has always to be translated into its distal position before the trigger button is unlocked.

It is desirable to trigger the retraction of the needle when the contents of the syringe have been entirely delivered to the patient, i.e. when the stopper has bottomed out in the syringe. Automatically triggering the retraction when the stopper exactly reaches the end of its travel is a problem due to tolerances when manufacturing the syringe and stopper. Due to these tolerances the position of the stopper at the end of its travel relative to the means triggering retraction is not repeatable. Consequently, in some cases the stopper would prematurely bottom out so the retraction would not be triggered at all. In other cases the retraction would be triggered before the stopper bottomed so residual medicament would remain in the syringe.

The retraction could automatically be triggered a certain amount of time or travel before the stopper bottoms out in the syringe. However this reliable retraction would be traded off for residual medicament in the syringe.

Thus, in a preferred embodiment the interlock sleeve is furthermore arranged to prevent release of the distal ground of the drive spring when in the distal position. This means, the drive spring remains distally grounded as long as the auto-injector is kept pressed against the injection site so the needle retraction can only start when the auto-injector is removed from the injection site and the interlock sleeve consequently returns into its proximal position and thus releases the distal ground. Full delivery of the medicament and reliable refraction are thus achieved by waiting for the user action of removing the auto-injector from the injection site.

A retraction sleeve may be axially movable arranged in the main body, wherein the drive spring is arranged inside the retraction sleeve with its distal end bearing against a distal end face and with its proximal end bearing against a thrust face of a decoupling member. At least one resilient wedge may be arranged at the proximal end of the retraction sleeve, wherein the main body has a respective recess for accommodating the resilient wedge when the retraction sleeve is in its proximal position. The interlock sleeve in its distal position may be arranged to support the resilient wedge from inside so as to prevent it from translating in distal direction. Thus, when the interlock sleeve is pressed against the injection site, the retraction sleeve is kept from retracting. Only after removal of the auto-injector from the injection site and consequent translation of the interlock sleeve into its proximal position the retraction sleeve may translate in distal direction and retract the needle into the main body.

A tubular syringe carrier may be arranged for holding the syringe and supporting it at its proximal end. Supporting the syringe at the proximal end is preferred over support at the finger flanges since the finger flanges are more frangible under load while the proximal or front end of the syringe is more robust. The syringe and the syringe carrier are arranged for joint axial translation. The syringe carrier is telescoped in the interlock sleeve, wherein at least one resilient second latch is arranged in the main body near the proximal end. In the as delivered state the resilient second latches extend inwards in a manner to prevent the syringe carrier from translating in proximal direction. The resilient second latches are arranged to be disengaged from the syringe carrier upon translation of the interlock sleeve in distal direction.

In a preferred embodiment at least one latch is provided for axially fixing the retraction sleeve in a maximum proximal position. The decoupling member is arranged to decouple the latch when being moved in proximal direction nearly into a maximum proximal position. When decoupled, the retraction sleeve is allowed to move in distal direction and retract the needle by means of the spring force which is no longer grounded at its distal end. Thus, retraction can only occur if the latches have been released and if the auto-injector has been removed from the injection site.

Preferably the plunger is arranged for pushing the syringe and/or the stopper in proximal direction. At least one, but preferably two or more resilient decoupling arms are arranged at the decoupling member. The decoupling arms exhibit inner ramped surfaces bearing against a first shoulder of the plunger in proximal direction. The resilient decoupling arms are supportable by an inner wall of the retraction sleeve in order to prevent the decoupling arms from being flexed outward and slip past the first shoulder. In this state the plunger may be pushed in proximal direction by the decoupling member pushing against the first shoulder in order to insert the needle and inject the dose. At least one aperture is arranged in the retraction sleeve allowing the decoupling arms to be flexed outward by the first shoulder thus allowing the first shoulder to slip through the decoupling arms in proximal direction. This may happen when the injection is at least nearly finished. The decoupled plunger allows the syringe and needle to be retracted since it is no longer bearing against the decoupling member.

The syringe may be arranged for joint axial movement with a syringe holder which is slidably arranged in the retraction sleeve. The syringe holder is provided with at least one, but preferably two or more resilient syringe holder arms arranged distally, the syringe holder arms having a respective inclined surface for bearing against a second shoulder, which is arranged at the plunger proximally from the first shoulder. The syringe holder arms are supportable by an inner surface of the main body in order to prevent them from being flexed outward. Thus, when the trigger button is pressed the spring force forwarded by the plunger does not yet press against the stopper but against the syringe for forwarding it. Consequently, a so called wet injection is avoided, i.e. the liquid medicament is not leaking out of the hollow needle before the needle is inserted. A widened portion is provided in the main body for allowing the syringe holder arms to flex outwards when the syringe holder has nearly reached a maximum proximal position thus allowing the second shoulder to slip through the syringe holder arms and to switch load of the drive spring from the syringe to the stopper. This allows for defining the moment to start injecting the medicament.

Usually the hollow needle is equipped with a protective needle shield for keeping the needle sterile and preventing it from being mechanically damaged. The protective needle shield is attached to the needle when the auto-injector or the syringe is assembled.

Preferably a cap is provided at the proximal end of the main body. A sheet metal clip is attached to the cap for joint axial movement and independent rotation. The sheet metal clip is arranged to extend through an orifice into the interlock sleeve when the cap is attached to the interlock sleeve. The sheet metal clip incorporates at least two barbs snapped into a circumferential notch or behind a shoulder of the protective needle shield. This allows for automatically engaging the sheet metal clip with the protective needle shield during assembly. When the cap is removed from the interlock sleeve in preparation of an injection the protective needle shield is reliably removed without exposing the user too high a risk to injure themselves.

The cap may be attachable to the main body by a screw connection. This allows for a low force removal of the protective needle shield.

The aperture in the retraction sleeve may extend at least almost to the position of the decoupling arms in the as delivered state up to their position at the end of dose. The aperture may be arranged to be angularly misaligned with respect to the decoupling arm when the retraction sleeve is in its proximal position so the plunger does not decouple from the decoupling member. The aperture and the refraction sleeve are also arranged to rotate so as to align the aperture with the decoupling arms upon translation of the refraction sleeve out of the proximal position in distal direction so the plunger and decoupling member decouple from each other thus allowing retraction of the plunger, stopper syringe and needle. This embodiment allows for starting the retraction at any point of the injection cycle.

The rotation into the aligned position may be achieved by a cam track arranged in the main body and a cam follower in the retraction sleeve. The cam track may be essentially parallel to a longitudinal axis of the auto-injector with a short angled section at its proximal end.

Alternatively the cam track may be arranged in the retraction sleeve and the cam follower in the main body.

The auto-injector may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
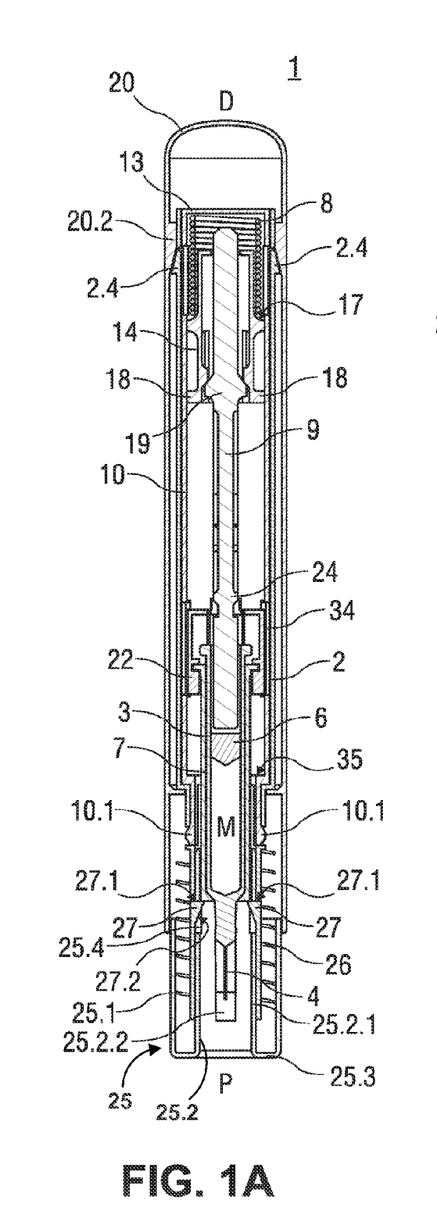
FIG. 1A are is a longitudinal section of an auto-injector with a single drive spring for advancing a syringe with a needle, injecting a dose of medicament and retracting the syringe and needle, the auto-injector as-delivered.
Figure 1B:
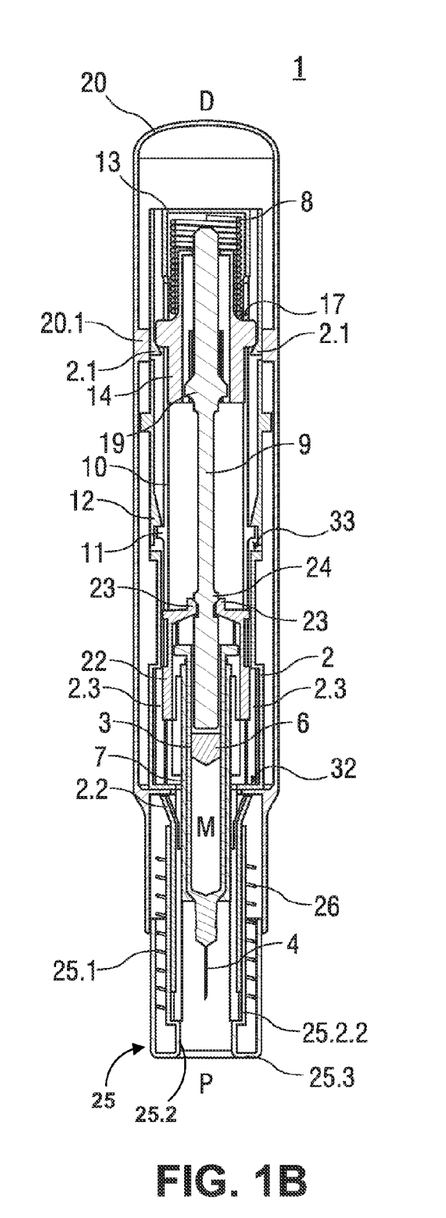
FIG. 1B illustrates the device of FIG. 1A where the longitudinal section shown is rotated approximately 90°.

FIGS. 1A and 1B shows two longitudinal sections in different section planes of an auto-injector 1, the different section planes approximately 90° rotated to each other. The auto-injector 1 comprises an elongate main body 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the main body 2 a retraction sleeve 10 is slidably arranged. Before the injection is triggered the retraction sleeve 10 is in a maximum proximal position and prevented from moving in distal direction D by means of stops 11 caught behind latches 12 in the main body 2. A distal end of the drive spring 8 bears against an end face 13 of the retraction sleeve 10. Due to the stops 11 and latches 12 the force of the drive spring 8 is reacted into the main body 2.

The proximal end of the drive spring 8 bears against a decoupling member 14 arranged around the plunger 9.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the retraction sleeve 10 in this situation so they cannot flex outward and slip past the first shoulder 19. In the as delivered configuration the decoupling member 14 is latched to the main body 2 by resilient first clips 2.1.

A trigger button 20 is arranged in the shape of a wrap-over sleeve button over the distal end D of the auto-injector 1 extending almost over the whole length of the auto-injector 1. The sleeve part of the trigger button 20 has a locking section 20.1 with a reduced diameter arranged to keep the clips 2.1 from flexing outwards in the as delivered configuration shown in FIG. 1B. Thus the decoupling member 14 is prevented from translating in proximal direction P.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIG. 1B the syringe holder arms 23 are supported by an inner surface of the main body 2 so they cannot flex outward and the second shoulder 24 cannot slip through. In order to support the syringe holder arms 23 at the main body 2 a respective number of apertures are provided in the retraction sleeve 10.

Two resilient clips 10.1 are arranged at a proximal end of the retraction sleeve 10. The main body 2 has two apertures arranged to accommodate the resilient clips 10.1 when the retraction sleeve 10 is in its proximal position.

A skin interlock sleeve 25 is arranged at the proximal end P. The skin interlock sleeve 25 has an outer wall 25.1 and an inner wall 25.2 with a space between them. The outer wall 25.1 and the inner wall 25.2 are connected to each other at the proximal end P by a front face 25.3 of the interlock sleeve 25. An inner wall portion 25.2.1 is telescoped in the main body 2 (see FIG. 1A). Another inner wall portion 25.2.2 is telescoped outside the main body 2. The outer wall 25.1 is telescoped in the wrap-over trigger button 20. An interlock spring 26 for biasing the interlock sleeve 25 in proximal direction P is hidden in the space between the inner wall 25.2 and the outer wall 25.1. The syringe carrier 7 is telescoped in the inner wall 25.2 of the interlock sleeve 25.

Two resilient second latches 27 are arranged in the main body 2 near the proximal end P. In the state as delivered the second latches 27 are relaxed and extend inwardly through respective apertures 25.4 in the interlock sleeve 25 in a manner to prevent the syringe carrier 7 from translating in proximal direction P by the syringe carrier 7 abutting against respective distal faces 27.1 of the second latches 27. The syringe carrier 7, the syringe 3 and the needle 4 can therefore not be forwarded when pushed by the plunger 9. Two outwardly biased resilient second clips 2.2 are arranged on the main body 2 distally from the resilient second latches 27. In the as delivered configuration the resilient second clips 2.2 are relaxed and extend outwardly in a manner to prevent the trigger button 20 from being translated in proximal direction P.

In order to start an injection the auto-injector 1 has to be pressed against the injection site, e.g. a patient's skin. For this purpose the auto-injector 1 is held by a caregiver or by the patient at the trigger button 20 which cannot translate relative to the main body 2 due to the clip 2.2. Instead the interlock sleeve 25 translates in distal direction D into the main body 2 (see FIGS. 2A & 2B). A proximal edge of the aperture 25.1 pushes against a proximal ramp 27.2 of the second latch 27 thereby flexing the second latch 27 outwards so the syringe carrier 7 comes clear of the distal faces 27.1 and may now translate in proximal direction P. At the same time a distal end of the inner wall portion 25.2.2 pushes the clip 2.2 inwards (see FIG. 2B) in a manner to allow the trigger button 20 to translate with respect to the main body 2.

Figure 2A:
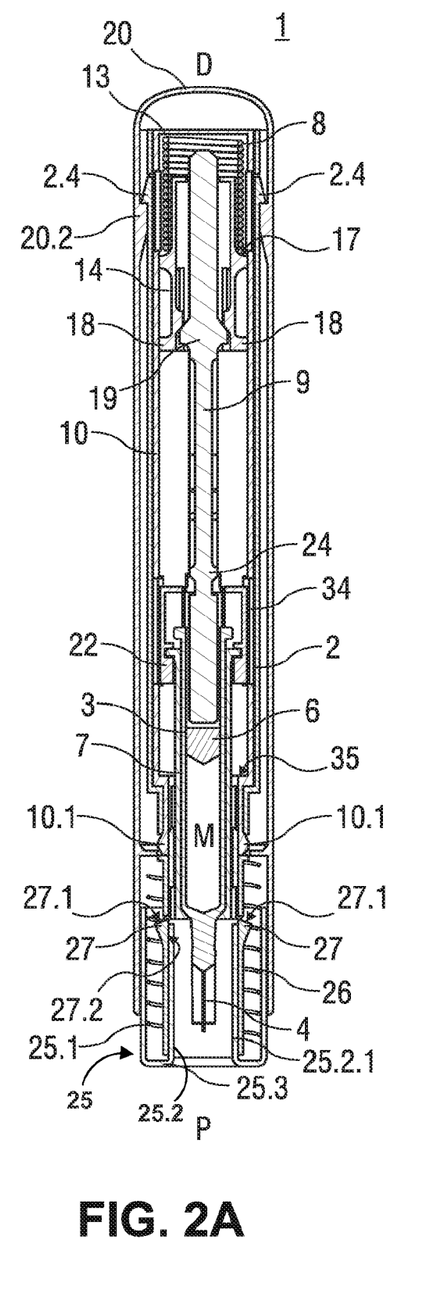
FIG. 2A is a longitudinal section of the auto-injector with a skin interlock shroud pressed against an injection site.

When translated into the main body 2 as in FIG. 2A distal end of the inner wall 25.2 of the interlock sleeve 25 supports the resilient wedges 10.1 from inside so they cannot be flexed inwards thus preventing the retraction sleeve 10 from translating in distal direction D.

If the auto-injector 1 is removed from the injection site at this stage without further pushing the trigger button 20 the interlock sleeve 25 will translate back into its proximal position under load of the interlock spring 26. The second latches 27 will flex inwards and block the syringe carrier 7 so the auto-injector 1 is in its as delivered state again. The clip 2.2 comes clear of the inner wall portion 25.2.2 and flexes outwards again thus blocking the trigger button 20 from translating in proximal direction P with respect to the main body 2.

If the pressure on the trigger button 20 in proximal direction P is continued, the trigger button translates in proximal direction P thus moving the locking section 20.1 into a position allowing the first clips 2.1 to flex outwards. This occurs by the decoupling member 14 sliding along ramps of the clips 2.1 under load of the drive spring 8. As the trigger button 20 approaches the end of travel it gets locked by engagement of catches 2.4 on the main body 2 and catches 20.2 on the trigger button 20 so it cannot translate back in distal direction D from this point. This prevents the main body 2 from floating inside the trigger button 20 during injection. Although the catches 20.2 and 2.4 are arranged near the distal end D the may likewise be arranged anywhere along the length of the sleeve of the trigger button 20.

Figure 2B:
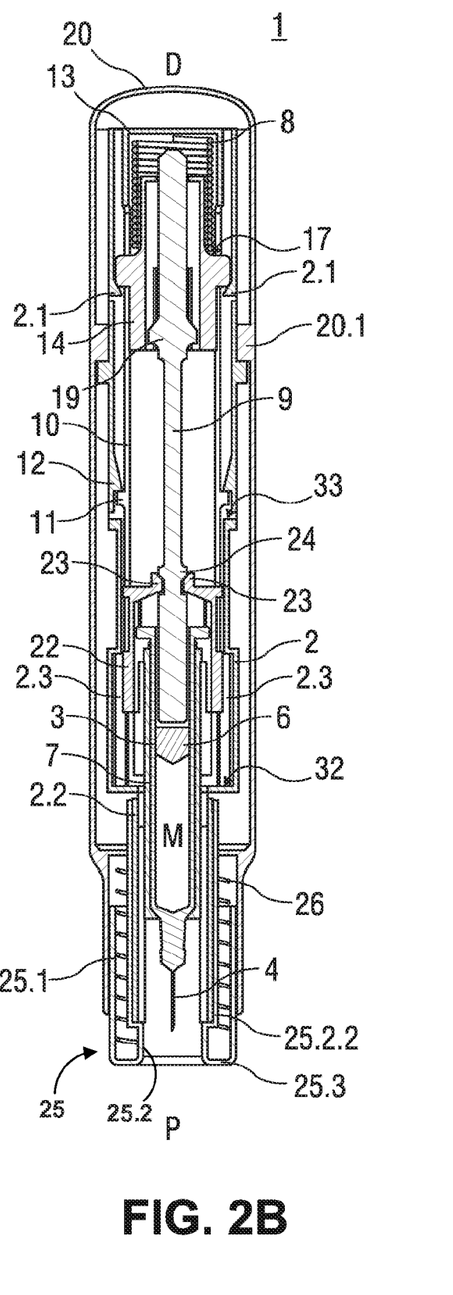
FIG. 2B illustrates the device of FIG. 2A where the longitudinal section shown is rotated approximately 90°

FIGS. 2A & 2B show the auto-injector 1 with the interlock sleeve 25 pushed into the auto-injector 1 and the trigger button 20 translated in proximal direction P and locked by the catches 20.2, 2.4.

The second shoulder 24 pushes the syringe holder 22, syringe carrier 7 and syringe 3 forward while no load is exerted onto the stopper 6. The hollow needle 4 appears from the proximal end P and is inserted into the injection site, e.g. the patient's skin.

The forward movement continues until the syringe holder 22 bottoms out at a first abutment 32 in the main body 2. The travel from the initial position up to this point defines an injection depth, i.e. needle insertion depth.

When the syringe holder 22 has nearly bottomed out the resilient syringe holder arms 23 have reached a widened portion 2.3 of the main body 2 where they are no longer supported by the inner wall of the main body 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 the decoupling member 14 has reached a position where it pushes against the latches 12 in a manner to decouple the refraction sleeve 10 from the main body 2. Thus the drive spring 8 is no longer grounded with its distal end in the main body 2 by the latches 12 so the drive spring 8 is trying to pull the retraction sleeve 10 in distal direction D.

Although the latches 12 are disengaged now, the retraction sleeve 10 may not yet slide in distal direction D because of the resilient clips 10.1 being kept from flexing inwards by the interlock sleeve 25 as long as the interlock sleeve 25 is in its distal position by the auto-injector 1 being kept pushed against the injection site.

If the auto-injector 1 is taken away from the injection site the interlock sleeve 25 will return to its proximal position (as in FIGS. 1A & 1B) under load of the interlock spring 26 so the resilient clips 10.1 are no longer supported from inside. Since the drive spring 8 tries to pull the retraction sleeve 10 in distal direction D, distal ramps of the resilient clips 10.1 move along proximal edges of the recesses in the main body 2 thereby flexing the resilient clips 10.1 inwards as the retraction sleeve 10 starts translating in distal direction D. The retraction sleeve 10 moves to a point where the decoupling arms 18 reach an aperture 34 in the retraction sleeve 10 so they are no longer kept from being flexed outward. The decoupling arms 18 are thus pushed outward by the first shoulder 19 pushing against its ramped surfaces so the first shoulder 19 can slip through in distal direction D. The decoupling member 14 can move a small distance further in proximal direction P in order to bottom out at a second abutment 33 and give ground to the drive spring 8 at its proximal end in the main body 2.

The retraction sleeve 10, still moving in distal direction D catches the syringe holder 22 with its front face 35 and takes it along in distal direction D. Thus the syringe 3 and needle 4 are retracted into a safe position inside the main body 2, e.g. into the initial position. The plunger 9, no longer bearing against the decoupling arms 18 is pulled back too.

The latches 12 and the stops 11 at the retraction sleeve 10 are not absolutely required. Retraction can be triggered by removal of the auto-injector 1 from the injection site alone. However, in the as delivered state, the stops 11 and latches 12 are part of a loop statically resolving the load of the drive spring 8, the loop comprising the decoupling member 14, the clips 2.1, the main body 2, the latches 12, the stops 11 and the retraction sleeve 10. Hence, in the as delivered state no load is exerted on the plunger 9.

If the auto-injector 1 is removed from the injection site prematurely, i.e. before the stopper 6 has bottomed out in the syringe 3, the retraction will start only when the syringe 3 is emptied. Despite the fact that the retraction sleeve 10 is released by the interlock sleeve 25 returning into its proximal position the decoupling member 14 and the plunger 9 have not yet reached the point where the decoupling arms 18 meet the aperture 34 of the retraction sleeve 10. Hence, the plunger 9 is still under load of the drive spring 8 and continues emptying the syringe 3. However, as the retracting sleeve 10 is released it starts translating in distal direction D and fills the gap between the front face 35 and the syringe holder 22. The actual retraction does not occur until the decoupling member 14 has bottomed out on the second abutment 33 thus giving ground to the proximal end of the drive spring 8. In the mean time the load of the drive spring 8 is resolved in a sub assembly loop consisting of the proximal end of the drive spring 8 pushing against the decoupling member 14, the plunger 9, the stopper 6, the syringe 3, the syringe carrier 7, the syringe holder 22 and the retraction sleeve 10 being pushed against by the distal end of the drive spring 8. In other words, this sub assembly is floating inside the auto-injector 1 while the syringe 3 is being emptied. The decoupling member 14 continues travelling in proximal direction P, releases the plunger 9 when meeting the aperture 34 and bottoms out on the second abutment 33. Hence, the proximal end of the drive spring 8 gets grounded in the main body 2 allowing the still expanding drive spring 8 and the retraction sleeve 10 to retract the syringe holder 22, the syringe carrier 7, the syringe 3 and the needle 4 into a needle safe position inside the auto-injector 1.

The invention claimed is:

1. An auto-injector for administering a dose of a liquid medicament, comprising:
    an elongate main body configured to contain a syringe comprising an attached hollow needle and a stopper for sealing the syringe and displacing the medicament, the main body having a distal end and a proximal end with an orifice to be applied against an injection site, wherein the syringe is positioned within the main body, the syringe configured to slide with respect to the main body during administration of a dose;
    a spring means, upon activation, configured to perform operations comprising:
        pushing the syringe towards the proximal end, wherein, in response to the pushing, the needle moves from a covered position inside the main body into an advanced position through the orifice and past the proximal end,
        operating the syringe to supply the dose of medicament, and
        retracting the syringe with respect to the main body with the needle into the covered position after delivering the medicament,
    activating means arranged to lock the spring means in a pressurized state prior to manual operation and, upon manual operation, configured to release the spring means for injection,
    wherein the spring means is a single drive spring in the shape of a compression spring arranged to be grounded at a distal end in the main body for advancing the syringe with the attached needle and for injecting the dose of medicament via a plunger and
    wherein a distal end of the drive spring is grounded in the main body,
    wherein the drive spring is arranged to have a ground of the drive spring in the main body switched from the distal end of the drive spring to a proximal end of the drive spring for retracting the syringe distally relative to the main body,
    wherein the activating means is arranged as a trigger button in the shape of a wrap-over sleeve button arranged over and that completely covers the distal end of the auto-injector, the trigger button extending almost over a whole length of the auto-injector,
    wherein the trigger button is arranged to release the drive spring upon translation in the proximal direction.

2. The auto-injector according to claim 1, wherein an interlock sleeve is telescoped with the proximal end of the main body, the interlock sleeve translatable in a longitudinal direction between a proximal position and a distal position and biased in the proximal direction in a manner to protrude from the main body in the proximal position, wherein in the proximal position of the interlock sleeve, the interlock sleeve is arranged to prevent translation of the syringe in the proximal direction from a retracted position of the syringe and wherein the interlock sleeve in the distal position of the interlock sleeve is arranged to allow translation of the syringe in the proximal direction.

3. The auto-injector according to claim 2, wherein a retraction sleeve is axially movable arranged in the main body, wherein the drive spring is arranged inside the retraction sleeve with the distal end of the drive spring bearing against a distal end face and with the proximal end of the drive spring bearing against a thrust face of a decoupling member, wherein at least one resilient clip is arranged at the proximal end of the retraction sleeve, wherein the main body has a respective recess for accommodating the at least one resilient clip when the retraction sleeve is in its proximal position wherein the interlock sleeve in its distal position is arranged to support the at least one resilient clip from inside so as to prevent the at least one resilient clip from translating in distal direction.

4. The auto-injector according to claim 3, wherein at least two resilient decoupling arms are arranged at the decoupling member, the at least two decoupling arms having inner ramped surfaces bearing against a first shoulder of the plunger in the proximal direction, wherein the at least two decoupling arms are supportable by an inner wall of the retraction sleeve in order to prevent the at least two decoupling arms from being flexed outward and slip past the first shoulder and wherein at least one aperture is arranged in the retraction sleeve allowing the at least two decoupling arms to be flexed outward by the first shoulder thus allowing the first shoulder to slip through the at least two decoupling arms in the proximal direction, wherein the plunger is arranged for pushing the syringe and/or the stopper in the proximal direction.

5. The auto-injector according to claim 4, wherein the aperture extends at least almost to the position of the at least two resilient decoupling arms in the as delivered state, wherein the aperture is arranged to be angularly misaligned with respect to the at least two resilient decoupling arms when the retraction sleeve is in its proximal position and wherein the aperture is arranged to rotate so as to align with the at least two resilient decoupling arms upon translation of the retraction sleeve out of the proximal position in distal direction.

6. The auto-injector according to claim 5, wherein a cam track is arranged in the main body and that a cam follower is arranged in the retraction sleeve, wherein the cam track is essentially parallel to a longitudinal axis of the auto-injector with a short angled section at its proximal end.

7. The auto-injector according to claim 5, wherein a cam track is arranged in the retraction sleeve and that a cam follower is arranged in the main body, wherein the cam track is essentially parallel to a longitudinal axis of the auto-injector with a short angled section at its proximal end.

8. The auto-injector according to claim 3, wherein at least one latch is provided for axially fixing the retraction sleeve in a maximum proximal position, wherein the decoupling member is arranged to decouple the at least one latch when being moved in the proximal direction nearly into a maximum proximal position, thus allowing the retraction sleeve to move in distal direction and retract the needle.

9. The auto-injector according to claim 3, wherein the syringe is arranged for joint axial movement with a syringe holder which is slidably arranged in the retraction sleeve, wherein the syringe holder is provided with at least two resilient syringe holder arms arranged distally, the at least two resilient syringe holder arms having a respective inclined surface for bearing against a second shoulder which is arranged at the plunger proximally from the first shoulder, wherein the at least two resilient syringe holder arms are supportable by an inner surface of the main body in order to prevent them from being flexed outward and wherein a widened portion is provided in the main body for allowing the at least two resilient syringe holder arms to flex outwards when the syringe holder has nearly reached a maximum proximal position thus allowing the second shoulder to slip through the at least two resilient syringe holder arms and to switch load of the drive spring from the syringe to the stopper.

10. The auto-injector according to claim 2, wherein a cap is provided at the proximal end of the main body, wherein a sheet metal clip is attached to the cap for joint axial movement and independent rotation, the sheet metal clip arranged to extend through the orifice into the interlock sleeve when the cap is attached to the interlock sleeve, wherein the sheet metal clip comprises at least two barbs snapped into a circumferential notch or behind a shoulder of a protective needle shield attached to the hollow needle.

11. The auto-injector according to claim 10, wherein the cap is attachable to the interlock sleeve by a screw connection.

12. The auto-injector according to claim 2, wherein at least one resilient second clip is arranged on the main body, the at least one second clip being biased so as to block the trigger button from being translated in the proximal direction when relaxed, wherein the interlock sleeve in the distal position of the interlock sleeve is arranged to push the at least one second clip against a bias of the at least one second clip so as to decouple it from the trigger button thus allowing translation of the trigger button in the proximal direction.

13. The auto-injector according to claim 2, wherein the interlock sleeve in the distal position of the interlock sleeve is arranged to prevent release of the compression spring grounded at the distal end in the main body.

14. The auto-injector according to claim 2, wherein a tubular syringe carrier is arranged for holding the syringe and supporting it at its proximal end, the syringe and the syringe carrier arranged for joint axial translation, wherein the syringe carrier is telescoped in the interlock sleeve, wherein at least one resilient second latch is arranged in the main body near the proximal end, wherein in an as delivered state the at least one resilient second latch extends inwards in a manner to prevent the syringe carrier from translating in the proximal direction, wherein the at least one resilient second latch is arranged to be disengaged from the syringe carrier upon translation of the interlock sleeve in distal direction.

15. The auto-injector according to claim 1, wherein at least one clip is arranged in the main body, wherein the trigger button comprises a sleeve, wherein the sleeve of the trigger button has a locking section with a reduced diameter arranged to prevent the at least one clip from flexing outwards in an as delivered configuration, wherein the at least one clip is arranged to lock the drive spring in the as delivered configuration, wherein the at least one clip is arranged to be unlocked under load of the drive spring by flexing outwards when the trigger button and the locking section are translated in the proximal direction.

* * * * *